United States Patent [19]

Seedhom et al.

[11] Patent Number: 4,668,233
[45] Date of Patent: May 26, 1987

[54] PROSTHETIC LIGAMENTS AND INSTRUMENTS FOR USE IN THE SURGICAL REPLACEMENT OF LIGAMENTS

[76] Inventors: Bahaa B. Seedhom, 75, Holt Park Crescent, Leeds, West Yorkshire, LS16 7SL, England; Kyosuke Fujikawa, Department of Orthopaedic Surgery, Keio School of Medicine, Tokyo, Japan

[21] Appl. No.: 628,835

[22] Filed: Jul. 9, 1984

Related U.S. Application Data

[63] Continuation-in-part of Ser. No. 580,437, Feb. 15, 1984, abandoned.

[30] Foreign Application Priority Data

Feb. 16, 1983 [GB] United Kingdom ............... 8304264

[51] Int. Cl.[4] .................................................. A61F 2/08
[52] U.S. Cl. ............................................ 623/13; 623/16; 128/92 R
[58] Field of Search ............... 3/1 B, 1, 1.9, 1.911; 128/92 C, 334 R; 623/16

[56] References Cited

U.S. PATENT DOCUMENTS

| 887,074 | 5/1908 | Depage | 128/334 R |
|---|---|---|---|
| 4,149,277 | 4/1979 | Bokros | 3/1.9 X |
| 4,209,859 | 7/1980 | Hoffman | 623/13 |

OTHER PUBLICATIONS

Linton, *The Modern Textile Dictionary*, 1957, pp. 389, 390 and 434.

Seedhorn et al., "The Leeds–Keio Artificial Ligament for Replacing the Cruciates", Imeche, c200/84, 1984, pp. 99–110.

*Primary Examiner*—Richard J. Apley
*Assistant Examiner*—Alan W. Cannon
*Attorney, Agent, or Firm*—Brooks & Kushman

[57] ABSTRACT

This invention relates to a new prosthetic ligament and a set of surgical instruments for use in the surgical replacement of a ligament and in particular for inserting a prosthetic ligament into the body.

The ligament in accordance with the invention comprises an elongate foraminous flexible strip, having at one end a pouch portion capable of receiving a bone plug and including an opening through which the bone plug may be inserted into the end portion, the pouch portion also including a closure or the like to prevent escape of the bone plug in a direction away from the center of the ligament.

The set of surgical instruments includes a new bone plug extractor which is adapted to sever the base of the bone plug from a host bone to allow complete separation of the bone plug.

12 Claims, 13 Drawing Figures

PROSTHETIC LIGAMENTS AND INSTRUMENTS FOR USE IN THE SURGICAL REPLACEMENT OF LIGAMENTS

This application is a continuation-in-part of pending prior application Ser. No. 580,437, which was filed on Feb. 15, 1984 in the names of Bahaa B. Seedhom, Julian G. Ellis, and Kyosuke Fujikawa now abandoned.

This invention relates to a new prosthetic ligament and a set of surgical instruments for use in the surgical replacement of a ligament and in particular for implanting a prosthetic ligament into the body.

Conventionally, damaged ligaments have been replaced by grafts from other tissues of the body. However, this is not totally satisfactory since extensive surgery is normally involved and the fixation of the replacement ligament is not always adequate. Prosthetic ligaments in the form of solid tubes of polyethylene have been used for constructing ruptured ligaments but again the fixation of these prosthetic ligaments was not satisfactory, and, further, their structure was not suitable. Carbon fibre was introduced in excess of five years ago as a possible prosthetic ligament. For implanting these, holes are drilled into the bones to be joined by the ligament and multifilament strands of carbon fibres are threaded through these holes, the strands being long enough to allow them to be simply knotted or tied around or within other devices to fix the ligament in position. Although the carbon fibre proves stronger than previous materials and growth of tissue is encouraged along the length of the fibres, such growth does not occur adequately when carbon fibres are used to replace intra-articular ligaments such as the cruciates of the knee joint. Furthermore, the holes which are required to be drilled in each bone are numerous and this involves large destruction of bone material which is not desirable. More particularly, control of the length of the ligament and its tension has proved very difficult, and anchoring of the ligament to the bone has not been achieved to any acceptable degree.

One ligament which has been proposed in U.S. Pat. No. 4,255,820 comprises a foraminous tube which has perforations of different size and density along its length. Column 2, lines 7 to 10 states "Zone A is constructed from a section 12 of tubular polyester fiber having densely woven fibers of small pore size to prevent tissue ingrowth. The pore size of section 12 is in the range of 2-10 microns." An internal central core is inserted into this area to help ensure that no tissue ingrowth occurs. Furthermore the ligament is flared at its ends to accommodate an autogenous bone graft but it would be very difficult to obtain a correspondingly shaped bone graft during an implantation procedure and securely to anchor the ligament to the bones with such an arrangement.

According to this invention there is provided a prosthetic ligament for implantation so as to extend between and to be anchored to two bones by means of a cylindrical bone plug at each bone, said ligament being an elongate, flexible element, one end of which includes a pouch portion capable of receiving a cylindrical bone plug, the pouch portion having a longitudinal slit through which the cylindrical bone plug may be passed to be accommodated within said pouch portion and an end closure whereby longitudinal movement of the bone plug out of the ligament is prevented, said ligament having perforations the size and distribution of which are substantially uniform along the length of the ligament except optionally over said end closure, the size of the perforations being such that ingrowth of both bone tissue and soft connective tissue is promoted where the ligament is anchored to bone by a bone plug, and ingrowth of soft connective tissue only is promoted where the ligament extends between said bones with the result that, after implantation, the ligament is subject to substantially continuous connective tissue ingrowth from and including one bone anchoring position to the other, thereby strengthening the ligament and its anchoring to each bone.

Accordingly, there is in effect a double anchoring of the ligament to the bones, a first anchoring being provided by the ingrowth of hard bone tissue where the ligament lies between bone surfaces about the bone plugs and a second anchoring being as a result of the ingrowth of soft connective tissue from and including the region of one bone plug between the bone surfaces, along the ligament between the two bones and to and including the second bone plug between the bone surfaces.

Preferably the ligament includes a coreless, tubular portion extending from said pouch portion in a direction toward said other end. Preferably the ligament, between said tubular portion and said other end, is in the form of a non-tubular strip of substantially uniform width.

The ligament is a perforated element of any biologically and mechanically compatible material and is preferably a polyester fabric with an open weave structure. Preferably the polyester is polyester is polyethylene terephthalate or a copolymer thereof, for instance, the material which is marketed under the trade mark "Terylene" in the U.K. and under the trade mark "Dacron" in the U.S.A. The weave of the fabric may be knitted open net but is preferably mock leno or leno woven, in which the weft threads are locked with respect to the warp threads.

Preferably the perforations have an area of at least 0.01 cm$^2$.

Preferably there are 10–40 perforations per square cm and more preferably 15–25 perforations per cm$^2$.

Each perforation is preferably in the range of 0.01 to 0.02 cm$^2$.

Preferably such a ligament is fixed within the body by threading the prosthetic ligament through a bore in each of the two bones to be joined by the ligament. Each bore comprises a reduced diameter portion which extends from the region at which the original ligament was attached to the bone and an enlarged diameter portion formed by removing a cylindrical plug of bone. The bone plugs are replaced into these enlarged diameter portions within the ligament, after the latter has been inserted, has been inserted thus securing the ligament between the bone plug and the rest of the bone. The perforations in the ligament which extend through the length of the ligament promote tissue ingrowth. The perforations in the region of the bone encourage bone growth which grows through the fabric of the ligament and joins the bone plug to the rest of the bone thus securing and giving a good fixation to the prosthetic ligament. The perforations within the same region promote soft tissue ingrowth where bone growth is incomplete or absent. This soft tissue ingrowth further enhances the strength of the fixation and allows a certain amount of give in the region of the ligament anchor. The perforations in the region between the two bones encourage soft connective tissue ingrowth only along the length of the ligament which can strengthen the ligament considerably.

The ligament may be formed from a length cut from a elongate strip which is inserted in the body and then trimmed (to remove any excess from the length of the ligament) once the ligament is fixed in place.

A particular useful structure for the prosthetic ligament is for the ligament to be formed from a tube of open weave polyester. In this case the end portion is formed by one end of the tube which is closed to prevent escape of the bone plug. The tube includes a longitudinal slit at each end of the ligament. At the pouch end of the ligament, the slit extends to the closed end of the pouch.

When the ligament is threaded into the bone, a cylindrical bone plug is inserted through the slit adjacent the closure and the other end of the ligament is pulled. This means that the bone plug is forced between the shoulder between the enlarged portion and the reduced diameter portion of the bore and the closure giving a well fixed location of the ligament. The other bone plug is then inserted and forced against the shoulder in the other bone thus securing the ligament to both bones.

Preferably, the closed end is formed by a row of stitches or by increasing the density of that region of the ligament at the end of the slit. This densly woven region will cause the ligament to resist stretch and hold in position about the end of the bone plug when forces are applied to the ligament during implantation.

Preferably, the end portion of the ligament which includes the pouch portion, also includes a terminal portion extending from the end closure and having attached thereto means whereby the ligament may be pulled, said terminal portion including a length of ligament between the point of attachment of said pulling means and said end closure, said length having perforations the size and distribution of which are substantially the same as the body of the ligament. Preferably, the pulling means comprise a cord attached to one end of said ligament, this cord being such that it may easily be threaded through the small bores.

Also in accordance with this invention there is provided a set of surgical instruments for use in the surgical replacement of an artificial ligament comprising a clamp with a guide for locating the axis along which a bore is required for fixation of a ligament, a reamer cooperable with the clamp for removing an annulus of bone dust, a bone plug extractor of the same outside diameter as the reamer, and a cylindrical drill bit guide of the same outside diameter as the reamer and bone plug extractor.

According to a further aspect of this invention a tool for guiding a cylindrical reaming tool along a predetermined axis to form a replaceable bone plug from a host bone comprises:

a first limb having a first pin at one end thereof, the pin being adapted to securely engage the bone;

a second limb having a guide for the reaming tool at one end thereof, said guide being oriented so that it will guide the reaming tool along a guiding axis which extends toward the first pin on the first limb;

at least two second pins adapted to securely engage the bone, the pins being mounted on the guide, said two second pins extending toward the first limb;

means for mounting the two second pins for adjustable rotational movement about the guiding axis of the guide to enable the second pins to be adjustably positioned to fit the contour of the bone;

means mounting the limbs for movement towards and away from each other and for applying a clamping force to the limbs whereby a bone may be engaged on opposite sides by said first pin and said second pins; and means for preventing the two limbs of said clamp from swivelling relative to each other to cause misalignment of the guide pin of the first limb and the axis of the guide in the second limb.

Preferably the means for mounting the limbs for movement towards and away from each other comprises at least one screw threaded member and a handle to tighten the screw thread.

When the clamp has been placed on the bone, a reamer is inserted in the cylindrical guide and is used to remove an annulus of bone dust from the bone. This locates the plug of bone to be removed and the clamp can now be removed. Occasionally the bone plug may break off and be retained within the reamer. Preferably the reamer includes a through hole into which a rod may be inserted to push the plug out of the reamer.

According to this invention a tool for extracting a cylindrical bone plug from a bone in which an annular channel has been formed to define the periphery of said bone plug, said tool being adapted to sever the base of said plug from the bone, the tool comprising:

a grippable handle portion at one end;

a wall portion at the other end, the wall portion defining a hollow, open-ended cylinder adapted to receive the bone plug;

a longitudinally extending slot formed in the cylindrical wall;

said wall being adapted to be received within said annular channel of said bone with the bone plug being receivable within the open-ended cylinder, said slot defining an arcuate void region of the annular space in the bone.

The bone plug is extracted by inserting the cylindrical wall into the annulus. A short, sharp blow is applied in the middle region of the extractor while the handle is gripped, the force being applied at a point in said middle region but on the side opposite to the slot. This severs the bone plug completely from the host bone.

Preferably the extractor includes a marker to indicate the correct area to be struck. More preferably this comprises a flattened bearing surface.

The bone plug extractor includes the grippable handle which must be gripped whilst the force is applied so that no bone damage occurs.

When the bone plug has been removed a cylindrical drill bit guide is placed into the cylindrical socket formed in the bone. The drill bit guide has a through hole for accommodating a drill bit which is introduced into the guide so that a reduced diameter bore is then drilled from the base of the cylinder to the other side of the bone at a region where the single pin of the clamp engages the bone. This region is selected to be as close as possible to the position where the original ligament was attached to the bone.

This process is then repeated with the other bone to which the ligament is to be attached, the same instruments being used again.

Thus a set of tools according to this invention includes an above-mentioned clamp, a reamer which cooperates with this clamp, a bone plug extractor of the same diameter as the annulus of the reamer, a rod which may be used with the bone plug extractor, and a cylindrical drill bit guide of the same diameter as the reamer and bone plug extractor.

A ligament in accordance with the invention may be used to replace the cruciate ligaments of the knee. It can also, in the form of, for instance, a flat strip, be used to replace the medial ligament of the knee, or other ligaments or tendons of other joints.

A prosthetic ligament and a set of surgical instruments and a method of inserting the ligament into the body will now be described by way of example only, with reference to the accompanying drawings, in which.

Figure 1:
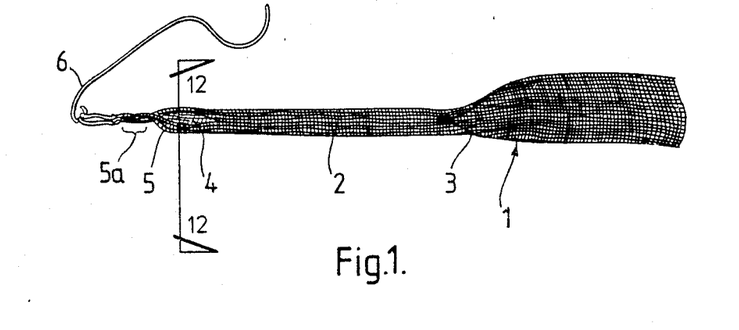
FIG. 1 is a perspective view of the prosthetic ligament.

An artificial ligament 1 comprises an elongate strip of open weave polyester. This fabric is Terylene and is a mock leno weave comprising a warp of 550 Decitex polyester yarn and a weft of twisted polyester yarn. The holes are 0.1×0.2 cm. There are fourteen to fifteen holes across the width of the strip, and twenty holes per cm$^2$.

The ligament is in the form of a tube 2 which has a slit 3 at one open end of the ligament 1 which extends to the open end edge of the ligament and a slit 4 at the other closed end of the ligament. The end of the slit 4 remote from the centre of the tube 2 is closed by a row or more of stitching or by dense weaving or in some other manner, to form a pouch capable of receiving a bone plug. As far as at the end of this row of stitching or densely woven section, the ligament extends further by a short portion 5a of the same open weave as the central portion 2. A threading cord 6 is attached to a position on this shorter 5a from the closure portion. The purpose of threading cord 6 is to allow the ligament to be pulled through the bores in the bone.

A bone plug may be inserted into the pouch through the slit 4. The stitching or densly woven section 5 forms a closure which prevents movement of the bone plug out of the pouch in a direction away from the centre of the ligament 1.

Figure 12:
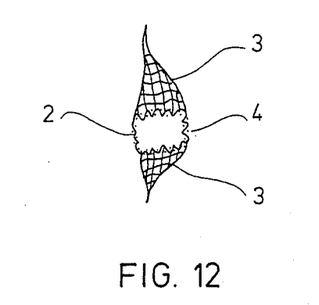
FIG. 12 is an enlarged sectional view taken substantially along line 12—12 in FIG. 1.

In order to illustrate the slit 4, the ligament has been shown in FIG. 1 with the slit 4 stretched openly with an exaggerated width at its center. Thus, as shown in FIG. 12, the slit forms an opening in only one side of the tubular portion of the ligament 1 whereby the ligament forms a pouch enclosure which can receive a bone plug.

Figure 2:
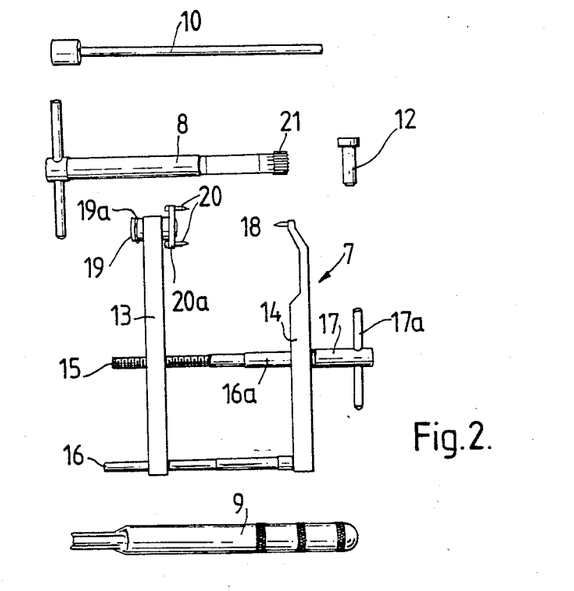
FIG. 2 is a perspective view of the set of surgical instruments used in the method.

A set of surgical instruments for use in the implantation of the ligament comprises a clamp 7, a reamer 8, a bone plug extractor 9, a push rod 10 and a drill bit guide 12.

Clamp 7 comprises two parallel limbs 13 and 14 interconnected by a main spacer rod 15 and an auxiliary rod 16. Main spacer rod 15, approximately centrally located in the clamp, is threaded from one end portion to a position lying about one third to one half of the length of the rod from that end portion. The threaded portion is in threaded engagement with a threaded bore located in limb 13 at the appropriate distances from the ends. The remainder of rod 15 is unthreaded and extends from the threaded portion through limb 14 to terminate in an enlarged head portion 17 carrying a handle 17a. For much of its length, this unthreaded portion of rod lies within a sleeve 16a which extends through limb 14 to which it is fixed. Within limb 14 sleeve 16a defines the bore through which rod 15 extends.

Auxiliary rod 16 is fixed at one end to limb 14 and extends through a bore or a slot in the other limb 13 for sliding movement therewithin.

The limb 14 includes a guide pin 18 extending perpendicularly from that end of the limb 14 remote from auxiliary rod 16. In use guide pin 18 engages the bone to locate the position of attachment of the ligament to the bone.

The other limb 13 has mounted on it a cylindrical guide 19 which is rotatably mounted within a bore in limb 13 and is provided with a circlip 19a to prevent movement of the guide out of its bore in limb 13. The other end of cylindrical guide 13 is in the form of an enlarged section or pin support 20a which in turn carries two pins 20. Extending through cylindrical guide 19 is a bore for receiving the reamer 8 such that reamer 8 will extend in a direction towards guide pin 18. The axes of guide pin 18 and said cylindrical guide are collinear.

Figure 3:
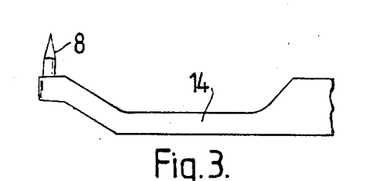

As best seen in FIG. 3, pins 20 are mounted on support 20a in a position offset from the bore extending through the guide 20 and at an angle to the axis of this bore. Guide 19 may be rotated within limb 13 so that the pins 20 describe the circumferential movement about the centre of the bore extending through guide 19. The position and orientation of the pins on guide 19 take account of the different contours of bone with which the clamp 7 may be used.

The reamer 8 passes through the cylindrical guide 19 and has sharp cutting edges 21, which are milled along its surfaces and form sharp teeth at the rim of the reamer, and a handle 22 which may be used to oscillate the cutting edges 21 to remove the bone dust.

Figure 4:
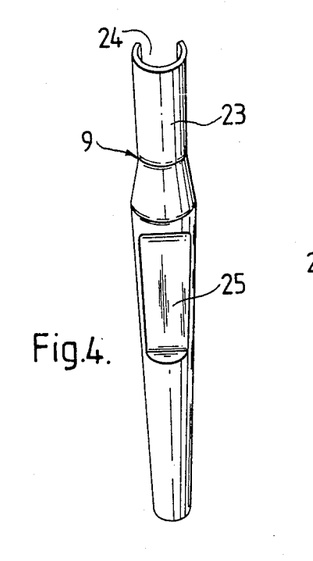
FIG. 4 is a perspective view of the bone plug extractor.

The bone plug extractor 9 includes at one end a cylindrical wall 23 which defines an open ended cylinder. At its other end the tool 9 includes a grippable handle 23a.

Figure 4A:
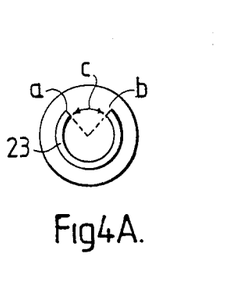
FIG. 4A is a view on that end of the bone plug extractor remote from the handle portion.

Extending from the edge of the wall 23 is a slot 24 which defines an arcuate void in the cylindrical wall of the same length as that of section 23. The angle circumscribed by the slot is about 80°. As shown in FIG. 4A, this angle c is subtended between the ends a, b of the slot and the centre of the circular portion of the wall 23.

On the opposite side of the bone plug extractor 9 to the slot 24 is a flattened bearing surface 25. This defines an area to be struck in order to sever a base of a bone plug being removed by the extractor tool 9.

The drill bit guide 12 is placed in the cylindrical hole created in the bone and is used as a guide for the drill bit to drill out the reduced diameter portion of the bore.

Figure 5:
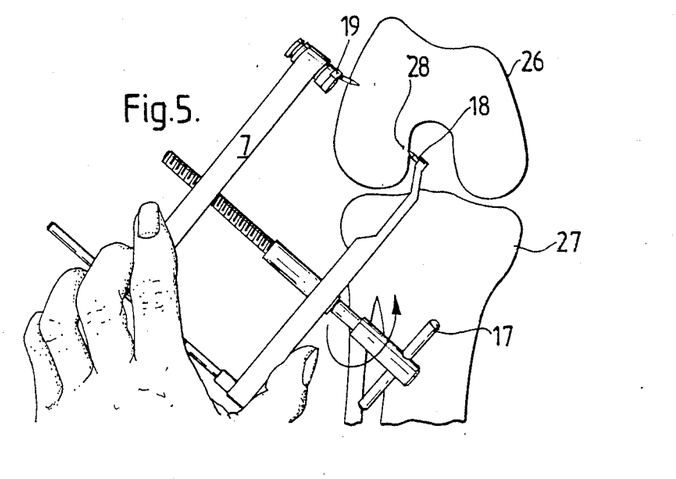
FIGS. 5 to 11 are representations (schematic only) of the steps of the method of replacing an anterior cruciate ligament in the knee.

The anterior cruciate ligament in the knee is connected to the femur 26 and the tibia 27. As showin in FIG. 5, the clamp 7 is placed around the femur 26 with the first guide pin 18 placed at a point within the region of attachment 28 where the original ligament was attached to the femur 26. The clamp is then rotated until the cylindrical guide 19 is at the opposite side of the femur 26. After adjusting the cylindrical guide such that the two pins engage the bone, the clamp 7 is then tightened up using handle 17a to locate the axis of the bore.

Figure 6:
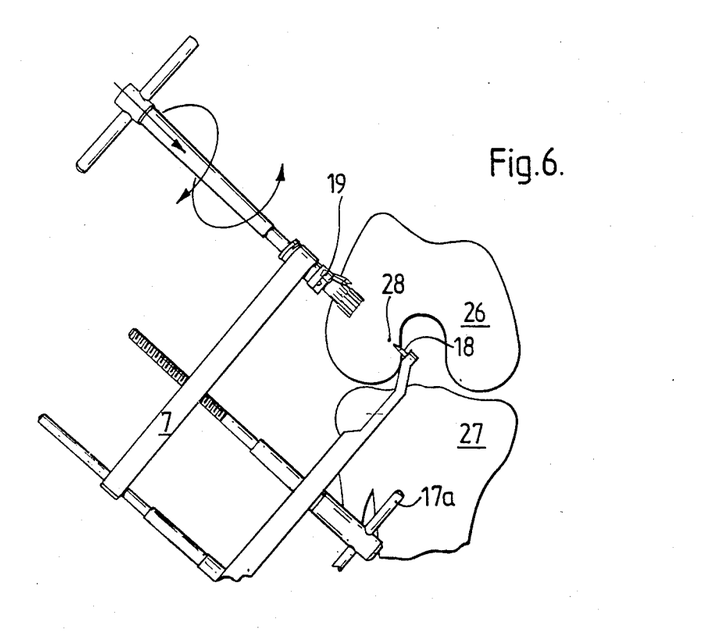
Figure 7:
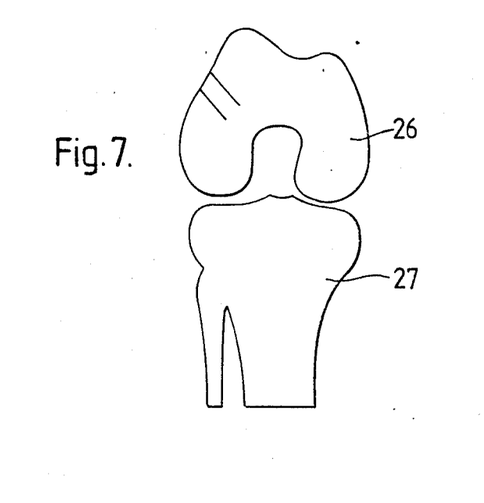

As shown in FIG. 6, the reamer 8 is then placed within the cylindrical guide 19 and the handle 22 is oscillated whilst applying a force along the axis of the reamer to remove an annulus of bone dust (FIG. 7). The reamer is then removed from the bone. In the infrequent possibility that the bone plug is removed within the reamer, the push rod 10 is inserted into the reamer to push the bone plug thereout.

Figure 8:
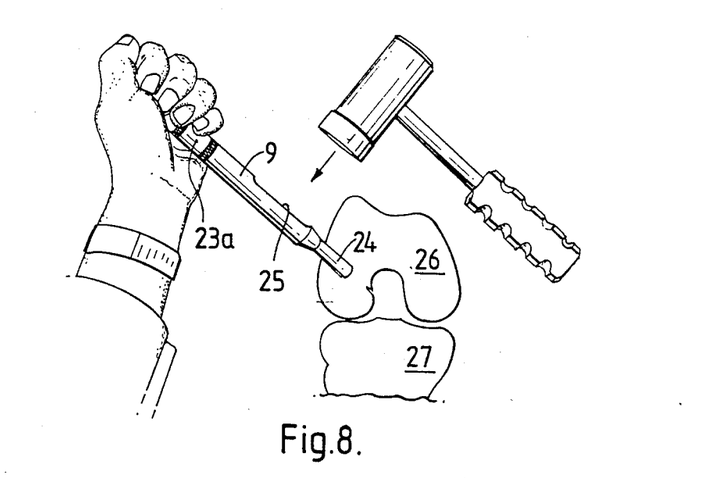

As shown in FIG. 8, the bone plug extractor 9 is then placed in the annulus defined in the femur 26. The gripping area 23a is held firmly to secure the bone plug extractor 9 firmly in place. A swift force is applied to the flattened surface 25 to remove the bone plug from the bone, by severing the base of the bone plug from the femur 26. The bone plug may be removed from the bone plug extractor 9 by inserting a rod into opening 24.

Figure 9:
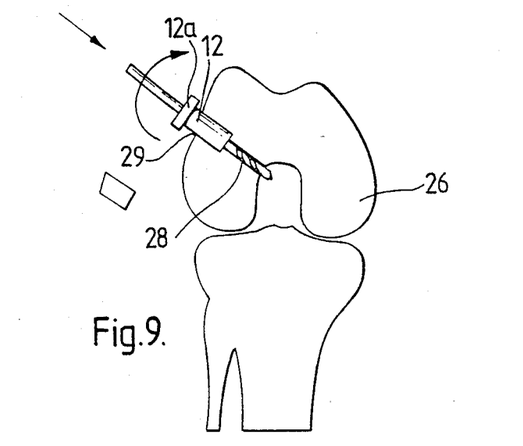

The drill bit guide 12 is then placed in the cylindrical hole left in the femur 26. The enlarged end 12a of drill bit guide 12 prevents the guide being pushed too far into the hole in the femur so that it is subsequently difficult to extract. A drill bit is then placed within the guide 12 to drill out the reduced diameter portion 28 of the bore 29 now formed through the femur 26.

Figure 10:
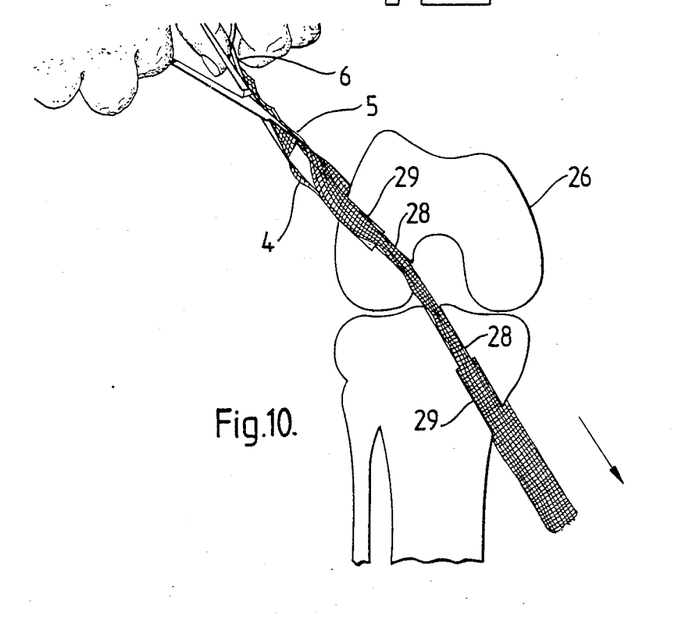

The procedure is then repeated in the tibia forming a similar bore in the tibia. The ligament 1 is then threaded through the two bores 29 using the cord 6. The bone plug from the femur 26 is then placed within the slit 4 in the ligament.

The other end of the ligament 1 is then pulled forcing the bone plug against the shoulder formed between the enlarged portion and the reduced diameter portion 28 by the closed end 5.

Figure 11:
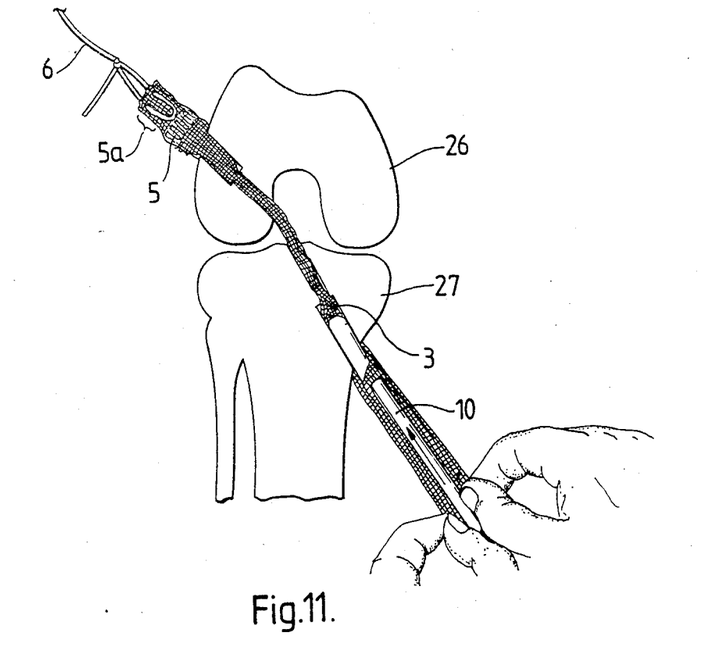

The bone plug from the tibia 27 is then forced into the opening 3, aided by a push rod. Thus the ligament 1 is secured by bone plugs within both the femur and tibia.

The ligament is stapled to the tibia and is then folded on itself. It is then stitched to itself and the periosteal tissue. The remainder of the ligament is then cut off.

At the end which emerges from the femur, the ligament is sutured to the periosteal tissue and the cord is clipped off. The remaining part of the ligament may be trimmed but at least some distance away from the closed end of the patch defined by the densly woven region.

Once the ligament is implanted within a patient, the ligament will be subject to tissue ingrowth as discussed above, thereby strengthening the ligament and also the anchoring of the ligament to the bones.

We claim:

1. A prosthetic ligament for implantation so as to extend between and to be anchored to two bones by means of a cylindrical bone plug at each bone, said ligament comprising an elongate, flexible element, one end of which includes a pouch portion capable of receiving a cylindrical bone plug, the pouch portion having a longitudinal slit through which the bone plug may be passed to be accommodated within said pouch portion and an end closure whereby longitudinal movement of the bone plug out of the ligament is prevented, said ligament having perforations the size and distribution of which are substantially uniform along the length of the ligament at least from and including said pouch to the other end of said ligament, the size of the perforations being such that ingrowth of both bone tissue and soft connective tissue is promoted where the ligament is anchored to bone by the bone plug, and ingrowth of soft connective tissue is promoted where the ligament extends between said bones, with the result that, after implantations, the ligament is subject to substantially continuous connective tissue ingrowth from and including one bone anchoring position to the other, thereby strengthening the ligament and its anchoring to each bone.

2. A prosthetic ligament in accordance with claim 1, wherein the ligament includes a coreless, tubular portion extending from said pouch portion in a direction towards said other end.

3. A prosthetic ligament in accordance with claim 2, wherein the ligament, between said tubular portion and said other end, is in the form of a non-tubular strip of substantially uniform width.

4. A prosthetic ligament in accordance with claim 1, wherein said ligament comprises a polyester fabric with an open weave structure.

5. A prosthetic ligament in accordance with claim 4, wherein said polyester is one of polyethylene terephthalate and a copolymer thereof.

6. A prosthetic ligament in accordance with claim 4, wherein the weave of said fabric is one of mock leno and leno woven whereby said fabric includes weft threads and warp threads locked with respect to each other.

7. A prosthetic ligament in accordance with claim 1, wherein said perforations have an area of at least 0.01 $cm^2$.

8. A prosthetic ligament in accordance with claim 7, wherein said distribution of said perforations is in the range 10 to 40 perforations per $cm^2$.

9. A prosthetic ligament in accordance with claim 8, wherein said distribution of said perforations is in the range 15 to 25 perforations per $cm^2$.

10. A prosthetic ligament in accordance with claim 7, wherein the size of said perforations is in the range 0.01 to 0.02 $cm^2$.

11. A prosthetic ligament in accordance with claim 1, wherein the said one end portion includes a terminal portion extending from said end closure and having attached thereto means whereby the ligament may be pulled, said terminal portion including a length of ligament between the point of attachment of said pulling means and said end closure, said terminal portion having perforations the size and distribution of which are substantially the same as the body of the ligament.

12. A prosthetic ligament in accordance with claim 11, wherein said means comprises a cord attached to said one end of said ligament.

* * * * *